(12) United States Patent
Riemer (10) Patent No.: US 11,760,968 B2
(45) Date of Patent: Sep. 19, 2023

(54) INCUBATOR, SAMPLE VESSEL, KIT AND METHOD FOR EXAMINING A SAMPLE MATERIAL

(71) Applicant: Testo SE & Co. KGaA, Lenzkirch (DE)

(72) Inventor: Joel Riemer, Breitnau (DE)

(73) Assignee: TESTO SE & CO. KGAA, Lenzkirch (DE)

( * ) Notice: Subject to any disclaimer, the term of this patent is extended or adjusted under 35 U.S.C. 154(b) by 0 days.

(21) Appl. No.: 16/759,030

(22) PCT Filed: Mar. 19, 2018

(86) PCT No.: PCT/EP2018/056854
§ 371 (c)(1),
(2) Date: Apr. 24, 2020

(87) PCT Pub. No.: WO2019/081069
PCT Pub. Date: May 2, 2019

(65) Prior Publication Data
US 2020/0277562 A1   Sep. 3, 2020

(30) Foreign Application Priority Data
Oct. 24, 2017 (DE) .......................... 102017124840.4

(51) Int. Cl.
*C12M 3/00* (2006.01)
*G01N 35/00* (2006.01)
(Continued)

(52) U.S. Cl.
CPC ............ *C12M 41/14* (2013.01); *C12M 23/28* (2013.01); *C12M 27/02* (2013.01); *C12M 37/04* (2013.01);
(Continued)

(58) Field of Classification Search
CPC ....... C12M 41/14; C12M 47/16; C12M 37/06
See application file for complete search history.

(56) References Cited

U.S. PATENT DOCUMENTS

| 4,827,944 | A | 5/1989 | Nugen |
| 5,275,299 | A | 1/1994 | Konrad et al. |

(Continued)

FOREIGN PATENT DOCUMENTS

| CN | 101061232 A | 10/2017 |
| DE | 3878066 | 7/1993 |

(Continued)

OTHER PUBLICATIONS

Thomson Scientific, London, GB, vol. 2006, No. 81, AN 2006-793579, Abstract N. 0, Retrieved from Database WPI [online], XP002782804 for JP 2006315106 A, Nov. 24, 2006.
(Continued)

*Primary Examiner* — Nathan A Bowers
(74) *Attorney, Agent, or Firm* — Volpe Koenig (57) ABSTRACT

An incubator (1) and its use for cultivating microorganisms and/or for carrying out a chemical reaction are provided. The incubator (1) has a sample vessel holder (3) for insertion of a sample vessel (4), a heating device (5) for changing a temperature in the sample vessel holder (3) and/or in a sample vessel (4) inserted into the sample vessel holder (3), and a sample-inactivating device (6) for inactivation of a sample (7) in a sample vessel (4) that is inserted into the sample vessel holder (3).

6 Claims, 2 Drawing Sheets

(51) Int. Cl.
*C12M 1/00* (2006.01)
*C12M 1/06* (2006.01)
*C12M 1/12* (2006.01)
*C12M 1/36* (2006.01)

(52) U.S. Cl.
CPC ............ *C12M 41/48* (2013.01); *C12M 47/16* (2013.01); *G01N 35/00584* (2013.01); *G01N 2035/00356* (2013.01)

(56) References Cited

U.S. PATENT DOCUMENTS

| | | | |
|---|---|---|---|
| 5,433,716 | A | 7/1995 | Leonardi et al. |
| 6,170,719 | B1 | 6/2001 | Wilkindon et al. |
| 9,562,214 | B2 | 2/2017 | Eberle et al. |
| 2005/0282268 | A1* | 12/2005 | Kagayama ............ C12M 41/46 435/288.7 |
| 2009/0111179 | A1* | 4/2009 | Hata .................. C12M 23/48 435/305.2 |
| 2010/0009433 | A1* | 1/2010 | Kimura ............... C12M 41/36 435/289.1 |
| 2011/0207209 | A1* | 8/2011 | Hammons ............ C12M 23/42 435/303.1 |
| 2011/0026310 | A1 | 10/2011 | Tumpner |
| 2011/0263010 | A1 | 10/2011 | Tumpner |
| 2016/0034805 | A1 | 12/2016 | Bhairavi |
| 2017/0073628 | A1 | 3/2017 | Zander et al. |
| 2017/0175069 | A1 | 6/2017 | Baker, Jr. et al. |
| 2019/0036633 | A1 | 12/2019 | Muhl et al. |

FOREIGN PATENT DOCUMENTS

| | | |
|---|---|---|
| DE | 69320686 | 4/1999 |
| DE | 202005021050 | 1/2007 |
| DE | 102010060634 | 5/2012 |
| DE | 102014106877 | 11/2015 |
| DE | 112009002620 | 3/2016 |
| DE | 102014019526 | 6/2016 |
| EP | 0877792 A1 | 11/1998 |
| EP | 2518137 | 10/2012 |
| EP | 3222709 | 9/2017 |
| JP | 2006315106 | 11/2006 |
| RU | 2547685 | 2/2015 |
| WO | 9820108 A1 | 5/1998 |
| WO | 2006001716 A1 | 1/2006 |
| WO | 2016059925 | 4/2016 |
| WO | 2016168803 | 10/2016 |

OTHER PUBLICATIONS

Thomson Scientific, London, GB, vol. 2016, No. 31, AN 2016-23869H, Abstract No. 0, Retrieved from Database WPI [online], XP002782805 for WO2016059925, Apr. 21, 2016.
Chinese Office Action dated Dec. 28, 2022 in related CN Appln No. 201880069311.X with English Translation.

\* cited by examiner

Fig. 1

INCUBATOR, SAMPLE VESSEL, KIT AND METHOD FOR EXAMINING A SAMPLE MATERIAL

TECHNICAL FIELD

The invention relates to an incubator and to the use thereof for cultivation of microorganisms and/or for performance of a chemical reaction, especially a biochemical reaction.

The invention further relates to a sample vessel for cultivation of microorganisms and/or for performance of a chemical reaction in an incubator and to the use of the sample vessel for analyzing a sample material present in a sample receiving chamber of the sample vessel.

The invention also relates to a set comprising an incubator and a sample vessel for cultivation of microorganisms and/or for performance of a chemical reaction.

The invention further relates to a method of analyzing a sample material, especially of detecting an intermediate and/or end product of a chemical reaction and/or a metabolite and/or a metabolism product and/or a nucleic acid and/or a nucleic acid sequence.

BACKGROUND

Incubators are apparatuses with which controlled incubation conditions (also referred to as culture conditions) can be created and maintained for various development and growth processes of microorganisms. More particularly, they thus serve to create and maintain a microclimate with controlled air humidity and temperature conditions.

Moreover, incubators can also be used to create particular reaction conditions for running and/or ending a chemical reaction.

In the food sector, samples (for example of foods and/or abrasive sponges) are taken and especially grown in a culture together with a cultivation medium in sample vessels designed as Stomacher bags. The bags can subsequently be transferred into a first incubator in order to be incubated therein. Subsequently, in general, some of the sample from the bag is plated out onto a sample vessel in the form of a selective agar plate and cultivated again in a second incubator. The agar plates can then be tested for growth of microorganisms, for example bacteria and fungi. Before the biological material is disposed of, it has to be inactivated, i.e. in particular killed off. An autoclave is generally used for the inactivation.

As already mentioned above, microorganisms are cultured in sample vessels such as petri dishes or cultivation bags. However, as a result, there is a considerable risk of the contamination of the laboratory and of the personnel working therein since the dishes in particular can easily run over and, moreover, many individual steps are required for performance of the cultivation, analysis and inactivation, and additionally personnel trained specially for the performance. Especially in the case of transfer of a microorganism from one sample vessel to a second sample vessel, there may be contamination since the sample vessels have to be opened manually for the purpose. It would therefore be desirable to avoid transfer of the biological material after inoculation of the cultivation medium.

Because the working steps involved in the entirety of cultivation, analysis and inactivation are quite complex, there is a high risk of contamination of the environment and nearby personnel. It is therefore desirable to provide an apparatus and a detection method by which the risk of contamination for the environment and personnel nearby is reduced or even eliminated.

Moreover, it is necessary that at least one instrument each is used for the cultivation and inactivation of the microorganisms. For instance, at least an incubator for cultivation and an autoclave or the like for inactivation is generally required. In the analysis, it may additionally be the case that a measurement apparatus for determination of an experimental parameter is required. It is therefore desirable to provide a single apparatus suitable for performing the cultivation and inactivation of a sample and optionally even the analysis of the sample, preferably without additional laboratory equipment.

SUMMARY

The objective addressed is therefore that of providing an incubator of the type specified at the outset, a sample vessel compatible with the incubator, and a method of analyzing a sample material, by which the disadvantages mentioned in each case are eliminated.

The solution to meeting this objective is achieved by the combination of one or more features as described herein. More particularly, what is thus proposed in accordance with the invention to meet this objective is an incubator of the type specified at the outset, having a sample vessel receiver into which a sample vessel can be inserted, having a heating device for changing a temperature in the sample vessel receiver and/or in a sample vessel inserted into the sample vessel receiver, and having a sample inactivation device for inactivation of a sample in a sample vessel inserted into the sample vessel receiver. By the apparatus of the invention, configured as an incubator, it is thus possible for the first time to undertake complex methods of cultivation of microorganisms and/or of performance of a chemical reaction with such reduced equipment since the incubator has a closable safety barrier which can prevent the sample to be analyzed from escaping in the activated or active state and leading to contamination. In one possible configuration, the sample inactivation device may be configured as an actuation device which, on actuation, activates and/or opens an inactivator of a sample vessel, especially an inactivation capsule.

A further solution to the abovementioned objective which is possibly of independent inventive quality, but may also be provided in combination with the aforementioned solution, is given by the features of the subordinate claim directed to an incubator. More particularly, what is thus proposed in accordance with the invention to meet this objective is an incubator of the type mentioned at the outset, having a sample receiver into which a sample can be introduced directly, having a heating device for changing a temperature in the sample receiver, and having a sample inactivation device for inactivating the sample in the sample receiver. The advantages of this configuration are therefore similar, as already set out in detail in the paragraph above, but there is a difference. The difference lies in the different disposal of the inactivated sample, since the sample here need not be disposed of together with the sample receiver, but separately therefrom. The sample receiver which can be or is disposed, for example, in an incubation chamber of the incubator may preferably be configured here so as to be removable from the further constituents of the incubator. This facilitates the emptying of the sample receiver. It may be particularly advantageous when the sample receiver takes the form of a tube. More preferably, the sample receiver may be one made at least partly from metal. It is thus possible to reuse the sample receiver very frequently since it can simply be cleaned and rinsed after use.

In an advantageous development, it may be the case that the incubator has a controller for establishing at least one program. The program that can be established may, for example, be an incubation program by which the incubation conditions for a microorganism can be established. Alternatively or additionally, the program may be an inactivation program by which inactivation conditions for a microorganism can be established. Alternatively or additionally, the program may be configured as a reaction program for establishing reaction conditions for performance of a chemical reaction. It is thus possible to better prevent incorrect operation of the incubator in that the controller can define the program to be conducted. This considerably simplifies the operation of the incubator since it is no longer necessary as a result for a user to independently set the required conditions that are to be generated by the incubator and possibly change them after a particular time has elapsed. It is thus possible to effect virtually completely automated running of cultivation, analysis and inactivation.

In a further advantageous configuration, alternatively or additionally to the advantageous configurations mentioned herein, it may be the case that the incubator has a safety lock set up such that a closure unit, after introduction of the sample vessel and closing of the sample vessel receiver, remains locked by the closure unit until an established program has ended and/or an opening code has been input by an authorized user. It is thus possible to better ensure that incorrect operation of the incubator, especially as a result of opening of the incubator, is ruled out, such that operation is possible even without specialist staff.

In a further advantageous configuration, alternatively or additionally to the advantageous configurations mentioned herein, it may be the case that the incubator has a safety lock set up such that a closure unit, after introduction of the sample into the sample receiver and closing of an incubation chamber and/or the sample receiver, remains locked by the closure unit until an established program has ended and/or an opening code has been input by an authorized user. It is thus likewise possible to better ensure that incorrect operation of the incubator, especially as a result of opening of the incubator, is ruled out, such that operation is possible even without specialist staff.

In a particularly advantageous development, it may be the case that the incubator has at least one measurement apparatus for performance of a measurement of at least one experimental parameter. More particularly, it may be the case that the measurement apparatus is or can be set up to perform a continuous measurement of at least one experimental parameter. It may be particularly preferable in an advantageous development when the measurement can be undertaken within a sample vessel inserted into the sample vessel receiver. Alternatively or additionally, it may be advantageous when the measurement can be undertaken within the sample receiver. It is thus possible for a user, independently and without further equipment, to conduct an analysis of a sample, preferably without having to remove the sample from the incubator and/or the sample vessel receiver.

In a further particularly advantageous development, it may be the case that the at least one measurement apparatus is set up to determine one or more experimental parameters selected from the group of optical density, color reaction, impedance, pH, gas composition, especially oxygen content and/or $CO_2$ content in liquid and/or supernatant, spectroscopic property, electrochemical property, reaction of a substrate and/or a chemical, fluorescence, luminescence, nucleic acids and/or a nucleic acid sequence, cell mass, peptides, proteins.

It may further be particularly preferable when the incubator has one measurement apparatus or multiple measurement apparatuses from the group of chromatography unit, especially high-performance liquid chromatography unit and/or thin-layer chromatography unit, mass spectrometer, lateral flow test unit, spectroscopy unit, especially Raman spectroscopy and/or NIR spectroscopy unit, fluorescence measurement unit, luminescence measurement unit, capilary electrophoresis unit, protein characterization unit, nucleic acid characterization unit, immunoassay unit, especially antibody assay unit, and/or immunobeads unit.

In order to be able to introduce a substance into the incubator and/or a sample vessel present therein and/or take a sample from the incubator and/or from the sample vessel preferably during the performance of an incubation program and/or without opening a safety lock, especially that already mentioned, it may be appropriate when the incubator has at least one opening for introduction of a chemical substance and/or a biological substance into the sample vessel and/or for selective taking of sample material, especially a sterile material sample, from the sample present in the incubator. Alternatively or additionally, it may further be advantageous when the opening is provided for introduction of a chemical substance and/or a biological substance into the sample receiver and/or for selective taking of sample material, especially a sterile material sample, from the sample receiver. In order to be able to prevent contamination of the space outside the incubator when taking a portion of the sample, it may preferably be the case that the opening has a chemical and/or biological and/or physical selection device for separating out microorganisms. The selection device may be configured, for example, as a filter, preferably as a filter membrane and/or a filter resin. Alternatively or additionally, the selection device may be configured as a purifying column. It may be particularly appropriate, alternatively or additionally to the advantageous configurations, in a further advantageous, development, when the opening is configured in a closure unit, especially that already mentioned herein. It may be particularly appropriate when the opening is tightly closable, especially in an airtight and/or watertight and/or pressure-resistant manner. This can be effected by a seal, for example.

In an advantageous development, it may further be the case that the incubator has a viewing window through which optical measurement on or in the sample is possible within the sample vessel receiver and/or within the sample receiver. It is thus possible to undertake a particularly simple, especially optical, measurement.

The attribute "within the sample vessel receiver" or "within the sample vessel" in the context of the application may mean that the measurement site is within the sample vessel receiver and/or within a sample vessel inserted therein, but that the measurement apparatus is arranged so as to perform a measurement, preferably an optical measurement, outside the sample vessel receiver and/or outside or within the sample vessel. For example, it may be advantageous when the sample vessel has a measurement apparatus disposed within the sample receiving chamber. The measurement apparatus may especially be configured as a sensor for measurement of physical and/or chemical properties.

Equally, "within the sample receiver" may mean that the measurement site is within the sample receiver, but that the measurement apparatus is arranged so as to perform a measurement, preferably an optical measurement, outside the sample receiver, especially in an incubation chamber, or within the sample receiver.

Thus, in an advantageous development, it may alternatively or additionally be the case that the incubator has an optical sensor for performing an optical measurement on the sample, especially wherein the optical sensor is disposed within or outside the sample vessel receiver. The arrangement of the measurement apparatus outside the sample vessel receiver has the advantage that simpler maintenance and/or calibration of the measurement apparatus, especially also during the performance of a measurement, is possible. Arrangement within the sample vessel receiver has the advantage that the measurement result is sometimes more accurate.

In a further advantageous development, it may alternatively or additionally be the case that the optical sensor is disposed within or outside the sample receiver. More particularly, the optical sensor may be disposed in the incubation chamber already mentioned.

In order to be able to achieve better mixing of the sample to be incubated, in a further advantageous development, it may be the case that the incubator has a shaker and/or stirrer unit for mixing the sample within the sample vessel and/or within the sample receiver.

It may further be particularly appropriate when the incubator has a detection device in order to detect a propagation process and/or biochemical activity of at least one microorganism within a sample vessel inserted into the sample vessel receiver. This enables better and simpler study of a growth of microorganisms present in a sample, preferably without needing to open and/or unlock the incubator and especially a safety lock or that already mentioned.

For the same reasons, it may additionally be particularly appropriate when the incubator has a detection device in order to detect a propagation process and/or biochemical activity of at least one microorganism within the sample receiver.

In a further advantageous development, it may be the case that the incubator has an injector unit for release of at least one substance into the sample vessel and/or the sample receiver. This enables, preferably during the performance of a program and/or in the locked state of the incubator, release of substances into the sample vessel and/or the sample receiver, in order, for example, to alter the incubation conditions and/or in order to trigger a chemical reaction, especially a detection reaction.

In a further advantageous development, it may be particularly appropriate when, by the program established by a controller, especially the controller or that already mentioned, one or more biological and/or chemical and/or physical incubation conditions can be established and/or varied. Preferably, the controller here can automatically set and vary the incubation condition envisaged depending on the program established. Possible incubation conditions preferably include one or more selected from the group of temperature, pressure, radiation, electron components, current, air humidity, acceleration, rotation and/or agitation speed, atmospheric components, pH and/or conductivity. It is thus possible by the incubator to cultivate a multitude of different microorganisms and/or to undertake a multitude of different chemical reactions, each by the establishment of different conditions.

In order to enable particularly reliable inactivation of the sample to be analyzed by the incubator, it may be the case, in an advantageous configuration, that the sample inactivation device inactivates the sample in one way or in multiple ways selected from the group of physical, mechanical, thermal, chemical, biological and/or radiation-generated inactivation. In a particularly preferred configuration, the sample inactivation device may be configured as at least one device selected from the group of autoclave, hot air sterilizer, gassing unit, irradiation unit, microwave unit, electron beam unit, ultrasound unit, vacuum unit, cavitation unit, shear force unit and/or inactivator release unit, especially for releasing a chemical and/or biological substance.

In an advantageous development, it may be the case that the heating device has a heating sleeve that forms the sample vessel receiver or is disposed on the inside of the sample vessel receiver. It may be particularly appropriate here when the heating sleeve surrounds the sample vessel in the inserted state. Thus, particularly uniform heating of a total volume of a sample vessel inserted into the sample vessel receiver is possible, such that it is possible to create the same incubation conditions throughout the sample vessel.

It may further alternatively or additionally be the case that the heating sleeve forms an incubation chamber, especially that already mentioned, or is disposed on an inside of the incubation chamber. The sample receiver here may be disposed or disposable in the incubation chamber.

Alternatively or additionally, in a likewise advantageous development, it may be the case that the heating device has at least one hotplate. It may be particularly appropriate here when the at least one hotplate is disposed in a base region of the sample vessel receiver and/or in a or the closure unit of the sample vessel receiver. This likewise enables very substantially homogeneous heating of a total volume of a sample vessel inserted into the sample vessel receiver. Alternatively or additionally, it may be appropriate when the incubator has a magnetic stirrer unit. Preferably, the magnetic stirrer unit may be disposed or formed in the base region.

Moreover, the heating device may alternatively or additionally also be set up to generate heating via air, radiation, ohmic heating or via a liquid.

In a further advantageous development, it may be the case that the incubator has an analysis unit set up to analyze, preferably automatically, whether inactivation of the sample was successful after performance of an inactivation program. It is thus possible to better control whether an inactivation step actually ran successfully or whether a further and/or different inactivation program should possibly be performed. It may be particularly appropriate here when opening of the sample vessel receiver and/or the incubator is enabled only in the event of successful inactivation, especially by preferably automatic release of a safety lock or that already mentioned previously.

In order to be able to prevent escape of the sample from the incubator, for example in the event of damage to the sample vessel, it may be advantageous when the sample vessel receiver and/or the incubation chamber can be closed tight. More particularly, it may be advantageous here when the sample vessel receiver and/or the incubation chamber is closable in a watertight and/or vapor-tight and/or airtight and/or pressure resistant manner. It is thus possible when performing any programs with different conditions to be able to prevent escape of the sample from the incubator.

In a further advantageous development, it may be the case that the incubator has a recognition device set up to prevent closing and/or activating of the incubator when a sample vessel incompatible with the incubator has been inserted into the sample vessel receiver or a compatible sample vessel has been inserted wrongly aligned into the sample vessel receiver. It is thus possible to prevent damage to a sample vessel inserted therein and/or to the incubator itself during the operation of the incubator.

It may be particularly appropriate when the incubator has at least one actuator device set up to open a capsule of the sample vessel, especially an inactivation capsule and/or a detection capsule, and/or to actuate an opening element and/or an opening the sample vessel. Preferably, the actuator device may be set up to open the capsule of the sample vessel without the incubator having been opened and/or the safety lock having been unlocked.

A further, independent solution to the objective stated at the outset is additionally provided by a sample vessel for cultivation of microorganisms and/or for performance of a chemical reaction in an incubator, having the features of the independent claim for a sample vessel. More particularly, the solution proposed here to the objective stated at the outset is a sample vessel for cultivation of microorganisms and/or for performance of a chemical reaction in an incubator, having a sample receiving chamber closable in a non-openable manner by a safety closure. The attribute "closable in a non-openable manner" in this connection may mean that the sample vessel, after closure, is openable only by destruction, i.e. improper use. In the event of proper use, it is therefore not possible to bring about opening of the sample vessel once it has been closed. It may therefore be particularly appropriate when the sample vessel is configured as a disposable article to be disposed of after a single use.

In order to be able to prevent escape of the sample to be analyzed from the sample vessel, in an advantageous development, it may be the case that the sample vessel is tightly closable by the safety closure. It may be particularly advantageous here when the sample vessel is closable in a watertight and/or vapor-tight and/or airtight and/or pressure-resistant manner by the safety closure. The sealing can preferably be effected here by a seal.

In order to enable mixing of multiple materials or substances within the sample vessel, preferably without opening them, in an advantageous development, it may be the case that the sample vessel has a magnetic stirrer bar. More particularly, it may be appropriate for the stirrer bar to be disposed in the sample receiving chamber, preferably at the base of the sample receiving chamber.

In an advantageous development, it may be the case that the sample vessel has at least one measurement apparatus for performance, especially continuous performance, of a measurement of at least one experimental parameter. Preferably, the measurement apparatus may be set up to perform a measurement within the sample vessel inserted into a sample vessel receiver. The attribute "within the sample vessel" in the context of the application may mean that the measurement site is effected within the sample receiving chamber, but that the measurement apparatus for performance of a preferably optical measurement is disposed outside the sample receiving chamber and/or outside the sample vessel. However, the measurement apparatus may also be disposed within the sample receiving chamber and/or the sample vessel.

In a particularly preferred configuration, it may be the case that the at least one measurement apparatus is set up to determine one or more experimental parameters selected from the group of optical density, color reaction, impedance, pH, gas composition, especially oxygen content and/or $CO_2$ content in liquid and/or supernatant, spectroscopic property, electrochemical property, reaction of a substrate and/or a chemical, fluorescence, luminescence, nucleic acids and/or a nucleic acid sequence, cell mass, peptides, proteins. It is thus possible to analyze a multitude of different experimental parameters. It may further be the case that multiple sample vessels are each equipped with different measurement apparatuses, for example as a set, in order thus to be able to undertake different detections in each case.

Alternatively or additionally, it may further be the case that the sample vessel has one measurement apparatus or multiple measurement apparatuses from the group of lateral flow test unit, capillary electrophoresis unit, protein characterization unit, nucleic acid characterization unit, immunoassay unit, especially antibody assay unit and/or immuno-beads unit. Preferably, the sample vessel has a lateral flow test unit activatable by an actuator device of an incubator.

In a further advantageous development, it may be the case that the sample vessel has at least one lock opening for introduction of a chemical substance and/or a biological substance into the sample receiving chamber and/or for selective taking of sample material, especially a sterile material sample, from the sample present in the sample receiving chamber. The term "sterile material sample" in this context may mean that the sample material taken from the sample receiving chamber does not contain any microorganisms outside the sample receiving chamber. The lock opening therefore makes it possible to take sample material from the sample receiving chamber without opening the safety closure.

It may be particularly appropriate here when the lock opening has a chemical and/or biological and/or physical selection device for separating out microorganisms. The selection device may especially be configured as a filter. The filter here may preferably be configured as a filter membrane and/or as a filter resin. Alternatively or additionally, the selection device may be configured as a purifying column. In this way, it is possible to ensure that there is no contamination by microorganisms outside the sample vessel, but at the same time to introduce and/or discharge material into/from the sample vessel via the lock. More particularly, it is thus possible to take sample material usable, for example, for an analysis to be performed outside the sample vessel.

In order to enable very simple handling, in order to facilitate introduction and/or discharge into/from the closed sample vessel via the lock, in an advantageous development, it may be the case that the lock opening is configured in the safety closure and/or as a stub or in a stub.

In order to be able to undertake a simple, preferably optical, measurement within the sample receiving chamber, in a further advantageous development, it may be the case that the sample vessel is at least partly cylindrical and/or that the sample vessel is at least partly transmissive, especially transparent. It may preferably be the case here that an outer shell of the sample vessel is configured to be at least partly transmissive and/or has a transmissive viewing window.

In a further advantageous development, it may be the case that the sample vessel has an inactivation capsule containing an inactivator that can be released into the sample receiving chamber by actuating an opening element. More particularly, it may be the case here that the inactivation capsule is disposed within the sample receiving chamber. It may further be appropriate when the inactivator is a sterilizing reagent. The opening element may preferably have been matched to the already aforementioned actuation device of an incubator such that the opening element can be actuated by the actuation device when the sample vessel is inserted into the incubator.

In order to be able to better prevent unwanted damage and escape of the contents, in a preferred configuration, it may be the case that the capsule has been produced from a flexible material. In order to enable the opening of the capsule, it may be appropriate for the opening element to be configured as a bolt or pin that penetrates a capsule wall or opens a capsule closure through actuation of the opening element. The opening element is preferably disposed within the capsule.

In an advantageous configuration, it may be the case that the sample vessel has a detection capsule having a detection device for detection of a chemical and/or biological substance in the sample held in the sample receiving chamber. The detection capsule here may preferably be disposed within the sample receiving chamber. The detection capsule may also be intended to detect an antigen and/or a nucleic acid and/or a nucleic acid sequence. The detection capsule may be openable by actuating an opening device, especially that already mentioned, and the detection device may be releasable into the sample receiving chamber. In a particularly preferred configuration, the detection capsule includes a lateral flow test that can be at least partly inserted into the sample receiving chamber by actuating the opening device. This enables a particularly easily performable and nevertheless reliable analysis of a sample without a user needing to introduce any materials or substances into the sample vessel, for example via the lock opening. The sample vessel therefore provides its own detection unit that can preferably even be initiated automatically, for example as part of a program that can be established in an incubator. The opening element is preferably disposed within the capsule.

In a further advantageous configuration, it may be the case that a reaction medium or a cultivation medium is provided in powder form in the sample vessel, which is liquefiable by addition of water and/or another solvent. The reaction medium may be or contain, for example, a buffer substance for establishing a pH. The cultivation medium may likewise contain a buffer substance. Alternatively or additionally, it may contain further substances needed for the growth of microorganisms, for example sugars, salts, amino acids and vitamins. It may be particularly advantageous when the medium contains a pH indicator, such as phenol red.

The providing of the medium in the sample vessel makes it possible to prevent a user from using a wrong medium, which in the worst case can even lead to a wrong result, for example when microorganisms are incompatible with the medium and therefore the result is wrongly negative even though the microorganism is present in the sample. By virtue of the preferably anhydrous powder form, it is additionally possible for the medium to have a long shelf life and for it to be made up only by addition of water or another solvent.

The invention also relates to a set comprising an incubator as described and claimed herein and a sample vessel as described and claimed herein, wherein the sample vessel is compatible with and/or configured with respect to the sample vessel receiver of the incubator. The set has the advantage that the user receives a sample vessel matched to the incubator, such that incorrect operation or improper use is better avoidable. The set may preferably also have multiple sample vessels that may be provided, for example, for performance of different analyses.

For performance of an analysis of sample material taken from the sample vessel, the set, in an advantageous configuration, may include a detection device for detection of a chemical substance and/or a biological substance in a sample. The detection device may preferably be executed separately here from the incubator and/or the sample vessel. The sample material may be a sterile material sample taken from the sample vessel, in which no microorganisms are present. In a particularly preferred configuration, the detection device may be configured as a disposable article, for example as a single test.

In an advantageous development, the incubator may have a guiding device in the sample vessel receiver, which interacts with a counterpart guiding device in the sample vessel such that the sample vessel can be inserted into the sample vessel receiver in a, especially in exactly one, defined insertion position. It is thus possible to even better prevent a user from wrongly inserting the sample vessel into the incubator or the user from using a sample vessel incompatible with the incubator.

In order to be able to conduct different analyses by the set, in a further advantageous development, it may be the case that the set contains multiple sample vessels each with a different medium. The medium may, for example, be a culture media and/or reaction media. It is possible here for a label to be provided on each of the sample vessels as to which analysis the sample vessel and/or the medium present therein is intended and suitable for. It is thus possible for a user to conduct a multitude of preferably different analyses on one sample.

A further independent solution to the objective stated at the outset is additionally achieved by a method according to the combination of features of the independent method claim. More particularly, the solution to the objective proposed by the invention is thus a method of analyzing a sample material, comprising the steps of:

providing a sample material to be analyzed and transferring the sample to a sample vessel, especially wherein the sample vessel is a sample vessel as described and claimed herein, introducing the sample vessel into a sample vessel receiver of an incubator, especially wherein the incubator is an incubator as described and claimed herein, closing the sample vessel receiver, performing an incubation program, especially wherein at least one incubation condition selected from the group of temperature, pressure, vacuum, radiation, electron components, current, humidity, acceleration, rotation and/or agitation speed, atmospheric components, pH, conductivity of a substrate is/are established and/or varied during the performance of the incubation program, performing an inactivation program, disposing of the sample vessel together with the sample material therein.

In a further independent solution, in addition, a method of the type specified at the outset is proposed, comprising at least the following steps:

providing a sample material to be analyzed and transferring the sample to a sample receiver of an incubator, as described and claimed herein, closing the sample receiver and/or an incubation chamber, performing an incubation program, especially wherein at least one incubation condition selected from the group of temperature, pressure, vacuum, radiation, electron components, current, humidity, acceleration, rotation and/or agitation speed, atmospheric components, pH, conductivity of a substrate is/are established and/or varied during the performance of the incubation program, performing an inactivation program, disposing of the sample material by emptying the sample receiver.

More particularly, the aforementioned method may be provided for detection of an intermediate and/or end product of a chemical reaction and/or a metabolite and/or a metabolism product and/or a nucleic acid and/or a nucleic acid sequence.

The method of the invention now for the first time enables performance of incubation and subsequent inactivation of a sample in just one sample vessel or one sample receiver. It is thus possible to reduce any risk of contamination when working with the sample to be analyzed, such that the analysis can be performed without further laboratory equipment.

The advantages already mentioned for the apparatus are additionally likewise applicable to the method of the invention and its advantageous developments.

In order to prevent the escape of the sample from the sample vessel, in an advantageous configuration, it may be the case that the sample vessel, after transfer of the sample, is closed in a non-openable manner. The sample vessel can preferably be closed here by a safety lock on the sample vessel.

In order to facilitate the disposal of an inactivated sample after performance of the inactivation step, the sample vessel can be disposed of in domestic refuse. This is possible because the sample vessel is closed in a non-openable manner even after inactivation of the sample, such that, given proper use, the opening of the sample vessel is impossible. The inactivation of the sample means that it is additionally harmless to man and the environment.

In an advantageous development, taking of sample material from the sample vessel or the sample receiver can be undertaken during and/or after the performance of the incubation program. In order to minimize any risk of contamination, it being possible to perform analysis even without laboratory equipment, it may be appropriate for the sample material to be sterile-filtered during the taking from the sample vessel or the sample receiver. Sample taking can alternatively or additionally also be undertaken after the performance of the inactivation program. By virtue of the sample taking, it is possible to undertake analysis of the sample material taken outside the sample vessel and/or outside the incubator. For this purpose, it is possible to undertake different analyses than in the closed sample vessel or in the closed incubation chamber, which sometimes allows even more exact analysis of the sample.

In a further advantageous development, it may alternatively or additionally be the case that a measurement of an experimental parameter of the sample material is performed within the sample vessel and/or within the sample receiver during and/or after the incubation program, or that a continuous measurement of an experimental parameter of the sample material is performed within the sample vessel and/or within the sample receiver during the incubation program. Thus, analysis of the sample material is also possible within the sample vessel and/or within the sample receiver without opening the sample vessel and/or the incubator. This can distinctly reduce the risk of contamination of the space around the incubator.

In order to be able to more effectively prevent improper opening of the incubator, in an advantageous development, it may be the case that the sample vessel receiver and/or the incubation chamber is locked during the performance of the incubation program and/or the inactivation program such that it cannot be opened. It may be particularly appropriate here when the lock is unlocked, especially automatically, as soon as the incubation program and/or the inactivation program has ended. In order to make the method even safer, it may alternatively or additionally further be the case that the lock is not unlocked until an authorized user inputs a release code.

In order to be able to further extend the range of possible analyses, in an advantageous configuration, it may be the case that at least one sample taken from the sample vessel and/or the sample receiver is subsequently analyzed outside the incubator. It may be particularly appropriate here when a detection device for detection of a chemical substance and/or a biological substance, especially a metabolite or metabolism product, is used for the purpose.

In order to create the best possible reaction and/or growth conditions, in a further advantageous configuration, it may be the case that a cultivation medium is provided or introduced in the sample vessel before or after transfer of the sample. It may be particularly advantageous here when the cultivation medium is in powder form and is liquefied by the addition of water and/or another solvent and then the sample is transferred into the sample vessel.

To further minimize any risk of contamination of the surrounding space and of the personnel in the vicinity, in an advantageous development, it may be the case that a or the opening in the incubator and/or a or the lock opening in the sample vessel is/are used for gas exchange and/or for pressure equalization. For this purpose, the opening and/or lock opening may have a valve, especially a pressure relief valve.

The invention further relates to the use of a sample vessel as described and claimed herein for analysis of a sample material present in a sample receiving chamber of the sample vessel, especially for detecting an intermediate and/or end product of a chemical reaction and/or a metabolite and/or a metabolism product, wherein the analysis is performed within an incubator as described and claimed herein. Preferably, the incubator and/or the sample vessel is closed during the performance of the analysis.

The invention also relates to the use of an incubator as described and claimed herein for cultivation and inactivation of microorganisms. More particularly, a measurement of at least one experimental parameter can be conducted here during the cultivation and/or the inactivation. In order to increase safety, the incubator can be locked during the cultivation and inactivation.

Preferably, the cultivation and/or inactivation takes place here in situ, i.e. especially without intermediate transport steps out of the incubator. It is thus possible to reduce or eliminate any risk of contamination of the environment as a result, for example, of a fracture or leak in the sample vessel.

The invention thus relates to an incubator and to the use thereof for cultivation of microorganisms and/or for performance of a chemical reaction, wherein the incubator has a sample vessel receiver for insertion of a sample vessel, a heating device for changing a temperature in the sample vessel receiver and/or in a sample vessel inserted into the sample vessel receiver, and a sample inactivation device for inactivation of a sample in a sample vessel that has been inserted into the sample vessel receiver in the use position. The sample vessel itself is not part of the incubator, but has merely been matched to it.

BRIEF DESCRIPTION OF THE DRAWINGS

The invention is now described in detail with reference to multiple illustrated working examples, but is not limited to these working examples. Further working examples result from the combination of the features of individual or multiple claims with one another and/or with individual or multiple features of the working examples.

The figures show.

DETAILED DESCRIPTION

Figure 1:
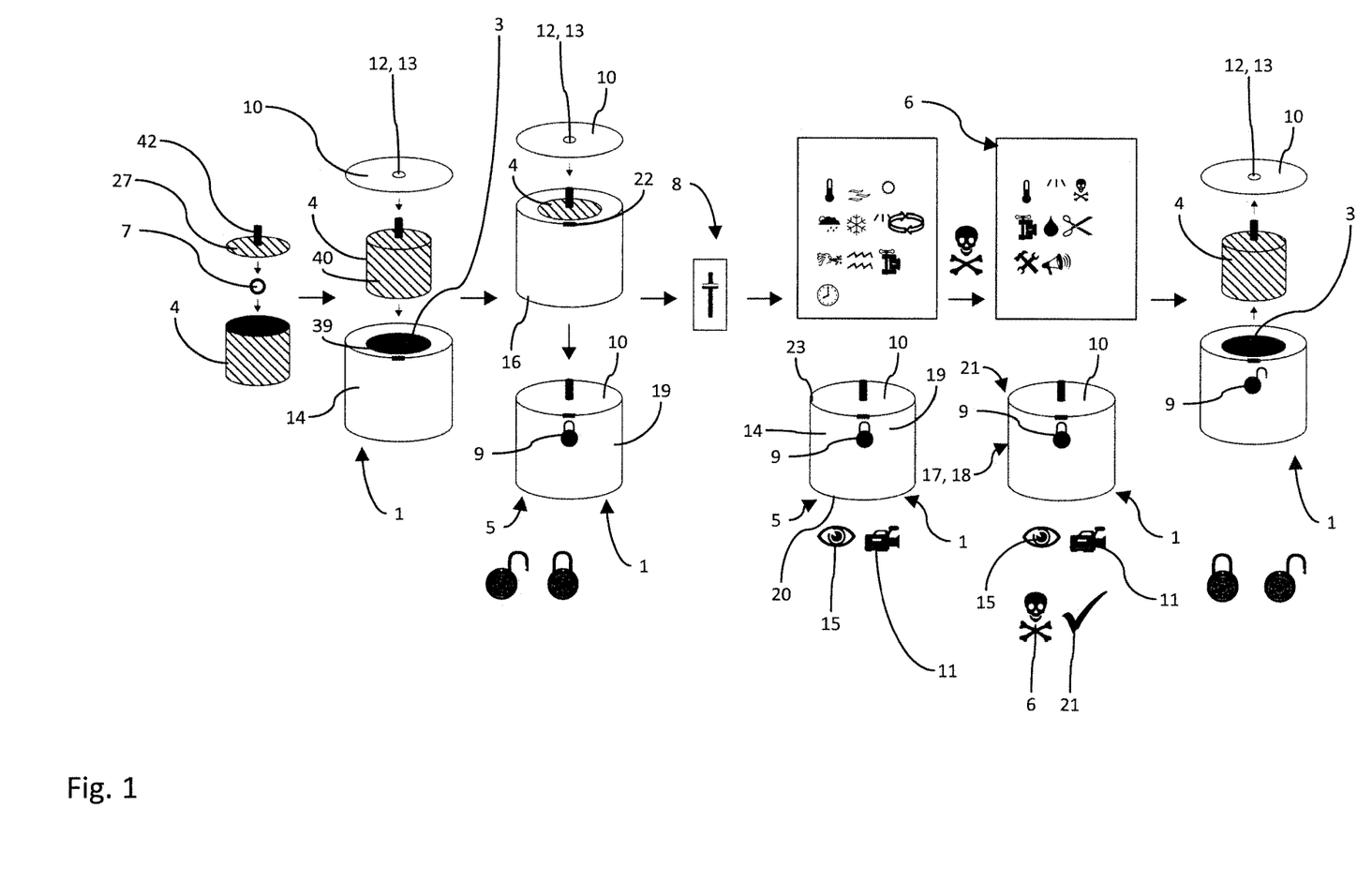
FIG. 1 a schematic diagram of a working example of the incubator of the invention and of the sample vessel of the invention, with additional indication of the individual steps of the method of the invention, FIG. 2 a configuration of a sample vessel of the invention in schematic view, FIG. 3 a transfer of a sample to the sample vessel, with the sample vessel open, FIG. 4 the closed sample vessel, with the sample in a medium in the sample receiving chamber, FIG. 5 an incubation step, with incubation of the sample present in the sample receiving chamber by generation of ideal reaction and/or growth conditions, FIG. 6 the triggering of a detection reaction by actuating an opening device, such that the sample is analyzed, and FIG. 7 an inactivation step, wherein actuating an opening element releases an inactivator from an inactivation capsule into the sample receiving chamber.

FIG. 1 shows an incubator referred to as 1 as a whole. The incubator 1 is intended for cultivation of microorganisms 2 and/or for performance of a chemical reaction. The chemical reaction may, for example, be a biochemical reaction.

The incubator 1 has a sample vessel receiver 3 into which a sample vessel 4 can be inserted. The incubator 1 also has a heating device 5 that serves to change a temperature in the sample vessel receiver 3. Thus, if a sample vessel 4 has been inserted into the sample vessel receiver 3, it is also possible to change the temperature therein. In addition, the incubator 1 has a sample inactivation device 6 intended for inactivation of a sample 7 in a sample vessel 4 inserted into the sample vessel receiver 3.

In a further embodiment of the incubator 1, not shown in the figures, an incubation chamber may be provided rather than the sample vessel receiver 3. A sample receiver disposed within the incubation chamber can be charged directly with a sample to be incubated. Thus, in this configuration, there is no intention to insert a sample vessel into the incubator, but rather to undertake incubation, analysis and inactivation of the sample within the sample receiver. In the description that follows, however, no further reference is made to this configuration variant. However, it is conceivable that the features described hereinafter are also employed in the embodiment with a sample receiver.

By the incubator 1, it is thus possible, preferably even outside a secure laboratory specially designed for the purpose, to undertake microbiological and/or biochemical analyses on a sample since the incubator 1 creates a dedicated sealed experimental chamber for the purpose, in which incubation and inactivation of the sample 7 can be performed. For instance, the incubator 1 can especially be used to undertake analyses on foods, for example in a restaurant or a food shop.

In order to be able to conduct a specific program for performance of a method by the incubator 1, preferably automatically, the incubator 1 has a controller 8. The controller 8 allows the establishment of various programs in order to be able to perform at least one incubation step and/or at least one inactivation step using an incubation and/or inactivation program. A user therefore has the opportunity to select a program for example directed specifically to a particular food and/or microorganism by the controller 8 in order thus to be able to undertake, preferably in an automated manner, incubation, analysis and inactivation of a sample 7.

The incubator 1 also has a safety lock 9 set up such that a closure unit 10 of the incubator 1 is openable only when a program established via the controller 8 has ended and/or when an authorized user inputs an opening code or undertakes another release activity. It may be particularly advantageous when the safety lock 9 is set up such that the closure unit 10, after introduction of the sample vessel 4 into the sample vessel receiver 3 and closure of the sample vessel receiver 3 by the closure unit 10, remains locked until an established program has ended, such that opening is not possible prior to performance of an inactivation step for inactivation of the sample 7 present in the sample vessel 4. It is thus possible to prevent contamination from occurring outside the incubator 1.

In order to be able to undertake analysis of a sample 7, the incubator 1 has at least one measurement apparatus 11. The measurement apparatus 11 is preferably set up to continuously undertake a measurement of at least one experimental parameter, especially while an established program is running. It may be particularly appropriate here when a continuous measurement is effected during an incubation program. The measurement of the at least one experimental parameter here can be effected within a sample vessel 4 inserted into the sample vessel receiver 3. This means that a measurement site is within the sample vessel 4 even though the measurement apparatus 11 is disposed outside and/or within the sample vessel 4. Moreover, it may, however, also be the case that the measurement apparatus 11 has a probe and/or sensor that extends into the sample vessel 4 in order to be able to undertake a measurement of at least one experimental parameter therein.

The measurement apparatus 11 is preferably set up to determine one or more experimental parameters selected from the group of optical density, color reaction, impedance, pH, gas composition, preferably with measurement of an oxygen content and/or a $CO_2$ content in liquid and/or in a supernatant, spectroscopic property, electrochemical property, reaction of a substrate and/or a chemical, fluorescence, luminescence, nucleic acids and/or a nucleic acid sequence, cell mass, peptides and/or proteins. It may therefore be appropriate when the incubator 1 has one measurement apparatus 11 or multiple measurement apparatuses 11 from the group of chromatography unit, especially high-performance liquid chromatography unit and/or thin-layer chromatography unit, mass spectrometer, lateral flow test unit, spectroscopy unit, especially Raman spectroscopy and/or NIR spectroscopy unit, fluorescence measurement unit, luminescence measurement unit, capillary electrophoresis unit, protein characterization unit, nucleic acid characterization unit, immunoassay unit, especially antibody assay unit, and/or immunobeads unit.

In order to be able to introduce a chemical substance and/or a biological substance into the sample vessel 4 and/or to be able to take sample material from the sample 7 present in the incubator 1 from the sample vessel 4, preferably during the performance of a program, the incubator 1 has at least one opening 12. The preferably closable opening 12 allows, by virtue of its configuration with a selection device 13, merely selective taking of sample material that does not contain microorganisms and is thus sterile. The selection device 13 may take the form, for example, of a filter. Particularly preferred filter configurations here may be a filter membrane and/or a filter resin. However, the selection device 13 may alternatively or additionally also be configured as a purifying column. Preferably, a separately configured opening 12 is provided in each case for the taking and introducing.

As apparent in FIG. 1, the at least one opening 12 is disposed in the closure unit 10. Thus, the opening 12 is very easy for a user to reach if he is conducting an experiment. The opening 12 may be tightly closable, for example by a sealing device. It may be particularly appropriate when the opening 12 is closable, especially closable by a sealing device.

The incubator 1 also has a viewing window 14 through which optical measurement on the sample 7 is possible. The sample 7 may be analyzed here within the sample vessel 4 inserted into the sample vessel receiver 3. For this purpose, the incubator 1 has an optical sensor 15 by which optical sensor 15 it is possible to perform an optical measurement on or in the sample 7. The optical sensor 15 may be disposed within or outside the sample vessel receiver 3 since measurements are also possible from outside the sample vessel receiver 3 via the viewing window 14.

In order to enable very good mixing of a sample 7, preferably with a medium 38, the incubator 1 has a shaker and/or stirrer unit 16.

In order to be able to detect a propagation process and/or biochemical activity of at least one microorganism 2 within a sample vessel 4 inserted into the sample vessel receiver 3, the incubator 1 has a detection device 17. The detection device 17 may be configured, for example, as part of the measurement apparatus 11, with a result being displayable directly to a user as to whether a propagation process is proceeding and/or biochemical activity is apparent.

The incubator 1 also has an injector unit 18 intended for release of at least one substance into the sample vessel 4. A user can therefore preferably introduce a chemical substance or a biological substance into the sample vessel 4 by the injector unit 18, for example during the performance of a program, without opening the incubator 1.

The controller 8 is set up to establish an establishment of one or more biological and/or chemical and/or physical incubation conditions. The controller 8 may be set up, for example, to be able to establish one or more incubation conditions from the group of temperature, pressure, radiation, electron components, current, air humidity, acceleration, rotation and/or agitation speed, atmospheric components, pH and/or conductivity. It is thus possible by the incubator 1 to conduct different chemical reactions and/or the cultivation of different microorganisms.

In order to be able to reliably inactivate a sample 7 present in a sample vessel 4 by the incubator 1, the sample inactivation device 6 may be set up to inactivate the sample 7 by one type or multiple types of inactivation method. The inactivation can be effected here preferably by physical, mechanical, thermal, chemical, biological and/or radiation-generated inactivation. The term "inactivation" may relate to killing of microorganisms, inactivation of viruses and/or rendering a chemical substance harmless.

The sample inactivation device 6 may be configured, for example, as at least one device selected from the group of autoclave, hot air sterilizer, gassing unit, irradiation unit, microwave unit, electron beam unit, ultrasound unit, vacuum unit, cavitation unit, shear force unit and/or inactivator release unit, especially for release of a chemical and/or biological substance.

In order to enable particularly uniform heating of a sample vessel 4 inserted into the sample vessel receiver 3, the heating device 5 has a heating sleeve 19 that lines the inside of the sample vessel receiver 3. The heating sleeve 19 therefore surrounds the sample vessel 4 in the inserted state, such that uniform release of heat is possible.

The heating device 5 also has a hotplate 20 that may be disposed in a base region of the sample vessel receiver 3 and/or in the closure unit 10 of the sample vessel receiver 3.

The incubator 1 has an analysis unit 21. The analysis unit 21 enables performance of an analysis as to whether an inactivation of the sample by the sample inactivation device 6 was successful. It may be particularly appropriate here when the analysis unit 21 is electronically coupled to the controller 8 and/or the safety lock 9, such that opening of the sample vessel receiver 3 is possible only in the case of successful inactivation. The safety lock 9 therefore remains closed until it has been detected by the analysis unit 21 that inactivation of the sample was successful.

If a sample vessel 4 is inadvertently damaged within the sample vessel receiver 3 of the incubator 1 in such a way that sample material 7 escapes, it is possible by a sealing element that enables watertight and/or vapor-tight and/or airtight and/or pressure-tight closing of the sample vessel receiver 3 with the closure unit 10 to prevent contamination of the surrounding space and of the personnel in the vicinity.

The incubator 1 has a recognition device 22 that recognizes when a sample vessel incompatible with the incubator 1 has been inserted into the sample vessel receiver 3 or a compatible sample vessel 4 has been inserted wrongly aligned. The recognition device here is thus able to prevent closure of the closure unit 10 and/or activation of the incubator 1. It is thus possible to avoid the risk of damage through the use of incompatible sample vessels or improper use of the incubator 1.

The incubator 1 has an actuator device 23 that can interact with an opening element 34 and/or an opening device 37 in the sample vessel 4. The actuator device 23 may therefore be operated from the outside in order to open an inactivation capsule 34 and/or a detection capsule 25 in the sample vessel 4 when the incubator 1 is closed and/or in operation.

FIG. 1 indicates a working example of a method of the invention for analysis of a sample material 7, wherein, in a first step, a sample 7 to be analyzed is transferred in a sample vessel 4. Subsequently, the sample vessel 4 is closed and introduced into the sample vessel receiver 3 of the incubator 1. The sample vessel receiver 3 of the incubator 1 is then closed by the closure unit 10 and locked by the safety lock 9. By the controller 8, it is then possible to perform an incubation program, the incubation conditions being freely adjustable or predefinable.

During the performance of the incubation program, the sample 7 within the sample vessel 4 can be analyzed by a measurement apparatus 11, 28. This can serve, for example, to detect growth of microorganisms 2 in the sample 7. If, for example, the growth of the microorganisms 2 exceeds a particular limit, it is necessary to dispose of a food from which the sample has been taken.

During the performance of the incubation step, it is possible to take sample material 7 from the sample vessel 4 in order to be able to undertake further analyses on a sample material 7 taken.

During the performance of the incubation program and a subsequent inactivation program, the sample vessel receiver 3 of the incubator 1 is locked, such that it is not openable by a user. After the performance of the incubation step, an inactivation program is conducted in order to achieve inactivation of the sample material 7 present in the sample vessel 4.

After the inactivation program has ended, the incubator 1 is unlocked, such that access to the sample vessel 4 in the sample vessel receiver 3 is possible and the sample vessel 4 can be removed.

Subsequently, the sample vessel 4 can be disposed of together with the sample 7 present therein. Owing to the inactivation of the sample 7 present, the sample vessel 4 can be disposed of in domestic refuse.

FIGS. 2 to 7 show a working example of a sample vessel 4 of the invention. The sample vessel 4 is intended for cultivation of microorganisms 2 and/or for performance of the chemical reaction, especially a biochemical reaction, in an incubator 1.

Figure 2:
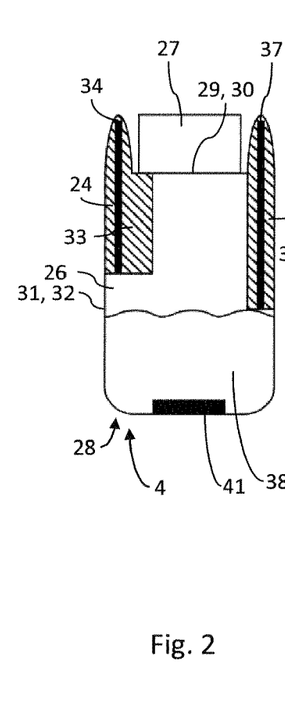

The sample vessel 4 has a safety closure 27 by which a sample receiving chamber 26 is closable in a non-openable manner. This means that the sample receiving chamber 26, after closure by the safety closure 27, is openable only by destruction of the sample vessel 4 since opening of the sample vessel 4 after closure thereof is not envisaged. It is thus possible to prevent improper use by a user, such that compliance with the requisite safety standards is easier and the risk of contamination of man and the environment is distinctly reduced.

In order to be able to use the sample vessel 4 in a maximum number of different incubation and/or inactivation programs, the sample vessel 4 is closable in a watertight and/or vapor-tight and/or airtight and/or pressure-resistant manner by the safety closure 27.

The sample vessel 4 may have a stirrer apparatus, for example in the form of a magnetic stirrer bar 41. It is thus more easily possible, for example, to dissolve a dried medium 38 held in the sample vessel 4 by addition of water or another solvent.

The sample vessel 4 may have a dedicated measurement apparatus 28, preferably set up for continuous performance of a measurement of at least one experimental parameter. The measurement apparatus 28 may be set up, for example, to determine one or more experimental parameters selected from the group of optical density, color reaction, impedance, pH, gas composition, especially oxygen content and/or $CO_2$ content in liquid and/or supernatant, spectroscopic property or electrochemical property, reaction of a substrate and/or a chemical, fluorescence, luminescence, nucleic acids and/or a nucleic acid sequence, cell mass, peptides and/or proteins. The sample vessel 4 may therefore have a measurement apparatus 28 or multiple measurement apparatuses 28 from the group of lateral flow test unit, capillary electrophoresis unit, protein characterization unit, nucleic acid characterization unit, immunoassay unit, especially antibody assay unit, and/or immunobeads unit.

In order to be able to introduce a chemical substance and/or a biological substance into the closed sample vessel 4, for example by an injector unit 18 of the incubator 1, the sample vessel 4 has a lock opening 29. In order to be able to prevent microorganisms from being able to escape inadvertently from the sample receiving chamber 26, the lock opening 29 has a selection device 30 for separation of microorganisms. The selection device 30 may be configured, for example, as a chemical and/or biological and/or physical selection device 30. It may be particularly appropriate when the selection device 30 takes the form of a filter, preferably a filter membrane and/or a filter resin. However, the selection device 30 may also be configured as a purifying column. The lock opening 29 is disposed in the safety closure 27 of the sample vessel 4. As apparent in FIG. 1, the lock opening 29 may be configured as a stub 42. A lock opening 29 in the form of a stub 42 may have the advantage of being guidable through an opening 12 formed in the closure unit 10 of the incubator 1 and hence, in use position, at least part of the stub 42 projects out of the sample vessel receiver 3 and/or is outside the sample vessel receiver 3. It is thus easier to perform the sample introduction and/or taking via the lock opening 29. The lock opening 29 may be closable, for example, by a seal. Alternatively or additionally, the lock opening 29 may be set up to perform a pressure equalization in the sample vessel 4. For this purpose, the lock opening 29 may have a valve, for example, especially a pressure relief valve.

The sample vessel 4 has a shape adapted to the sample vessel receiver 3 of the incubator 1. It may be particularly appropriate here when the sample vessel 4 has an at least partly cylindrical configuration. The sample vessel 4 has at least one transmissive viewing window 32, such that optical measurement is possible on or in a sample material 7 present in the sample vessel 4 by a measurement apparatus 11, 28 disposed outside the sample vessel 4. The viewing window 32 is preferably formed in an outer shell 31 of the sample vessel 4.

The sample vessel 4 has an inactivation capsule 24 disposed within the sample receiving chamber 26. The inactivation capsule 24 contains an inactivator 31 that may take the form, for example, of a sterilizing reagent. As a result of the actuation of an actuation device 23 in the incubator and/or an opening element 34 in the sample vessel 4, the inactivator 33 can be released from the inactivation capsule 24. The actuator device 23 here can actuate the opening element 34, such that it penetrates a capsule wall and/or opens a capsule closure 35. The opening element 34 is preferably configured as a bolt or a pin disposed within the inactivation capsule 24. The capsule wall is of flexible configuration, such that it establishes a certain puncture resistance on the one hand and easy opening is achievable by the opening element 34 on the other hand.

The sample vessel 4 also has a detection capsule 25 disposed within the sample receiving chamber 26. The detection capsule 25 contains a detection device 36 for detecting a chemical and/or biological substance. It may be particularly appropriate here when the detection capsule 25 is intended for detection of an antigen and/or a nucleic acid and/or a nucleic acid sequence. The detection capsule may be openable by actuating an actuator device 23 and/or an opening device 37. By actuating the actuation device 23, it is also possible to actuate the opening device 37, such that the detection device 36 is releasable into the sample receiving chamber 26. The detection capsule 25 here has been produced from a flexible material. This has the advantage that it is puncture-resistant on the one hand and is easily openable by the opening device 37 on the other hand. The opening device 37 is preferably configured as a bolt and/or pin. It may be particularly appropriate when the detection capsule 25 includes a lateral flow test that can be introduced at least partly into the sample receiving chamber 26 by actuating the opening device 37. The detection device 36 may alternatively or additionally also be a chemical that starts a detection reaction. A detection reaction may relate here, for example, to a detectable color change.

FIGS. 1 to 7 show individual method steps performable using the sample vessel 4.

Figure 3:
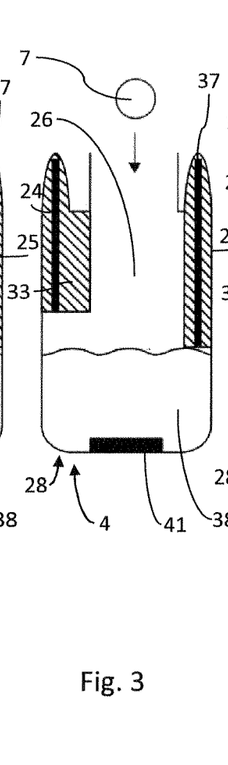

In FIG. 3, sample material 7 is first introduced into the sample receiving chamber 26 of the sample vessel 4.

Figure 4:
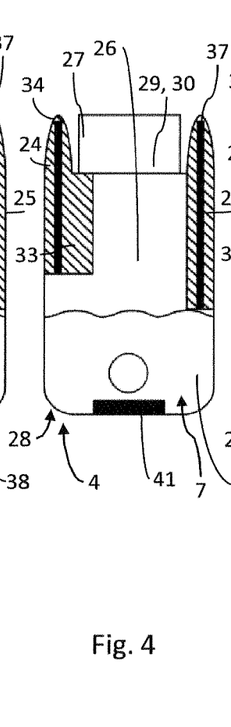

After the sample material 7 has been introduced into the sample vessel 4, the safety closure 27 is closed and locked, such that subsequent opening is no longer possible (cf. FIG. 4).

Figure 5:
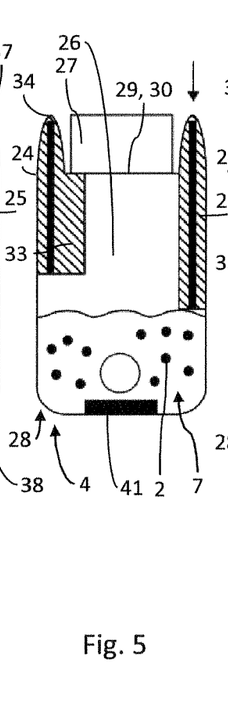

As shown in FIG. 5, there is subsequently an incubation step in which ideal reaction and/or growth conditions can be established by a controller 8.

Figure 6:
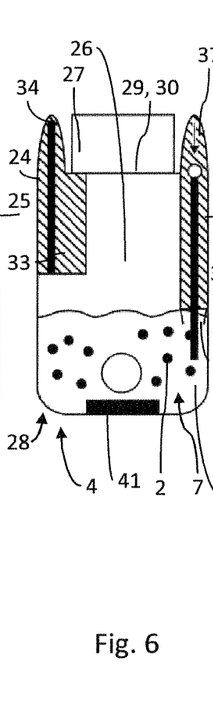

FIG. 6 shows a detection step. By actuating the opening device 37, a detection device 36, especially a lateral flow assay, is initially released into the medium 38, with opening of a capsule closure 35 by actuation of the opening device 37.

Figure 7:
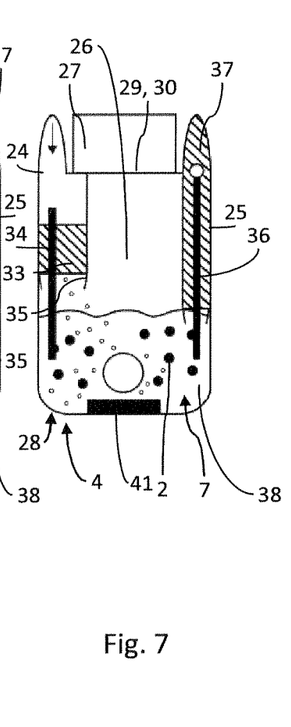

After performance of the detection that may result, for example, in a color change, as shown in step 7, an inactivation step is undertaken. By actuation of the opening element 34, this opens the inactivation capsule 24 at its capsule closure 35 in that the opening device 34 penetrates the capsule wall. Subsequently, the inactivator 33 present in the inactivation capsule 24 can be released into the sample receiving chamber 26 in order to inactivate the sample 7 present therein and the microorganisms 2 present therein.

Subsequently, the entire sample vessel 4 can be disposed of.

In order to be able to prevent the introduction of an incompatible sample vessel 4 or a compatible sample vessel 4 in the wrong alignment into the sample vessel receiver 3 of the incubator 1, the sample vessel receiver 3 has a guiding device 39, and the sample vessel 4 a compatible counterpart guiding device 40. By the guiding device 39 and the counterpart guiding device 40, it is possible to define a particular alignment of the sample vessel 4 on introduction into the sample vessel receiver 3. Thus, incorrect insertion of the sample vessel 4 into the sample vessel receiver 3 is ruled out. Especially in the case of performance of a sample vessel movement within the incubator 1, in the event of improper insertion of the sample vessel 4 into the sample vessel receiver 3, there may be damage to the sample vessel 4 and hence escape of sample material.

LIST OF REFERENCE NUMERALS 1 incubator
2 microorganism
3 sample vessel receiver
4 sample vessel
5 heating device
6 sample inactivation device
7 sample/sample material
8 controller
9 safety lock
10 closure unit
11 measurement apparatus
12 opening
13 selection device
14 viewing window
15 optical sensor
16 shaker/stirrer unit
17 detection device
18 injector unit
19 heating sleeve
20 hotplate
21 analysis unit
22 recognition device
23 actuator device
24 inactivation capsule
25 detection capsule
26 sample receiving chamber
27 safety closure
28 measurement apparatus
29 lock opening
30 selection device
31 outer shell
32 viewing window
33 inactivator
34 opening element
35 capsule closure
36 detection device
37 opening device
38 medium
39 guiding device
40 counterpart guiding device
41 magnetic stirrer bar
42 stub

The invention claimed is:

1. An incubator (1) for at least one of cultivation of microorganisms (2) or performance of a chemical reaction, the incubator comprising:
a sample vessel receiver (3) into which a sample vessel (4) is insertable;
a heating device (5) for changing a temperature in at least one of the sample vessel receiver (3) or in a sample vessel (4) inserted into the sample vessel receiver (3);
a sample inactivation device (6) for inactivation of a sample (7) in a sample vessel (4) inserted into the sample vessel receiver (3);
an analysis unit (21), comprising at least one measurement apparatus (11) having a sensor or probe extending into the sample vessel (4), to determine if the inactivation of the sample by the sample inactivation device (6) was successful; and
a closure unit (10) comprising a safety lock (9), wherein after introduction of the sample vessel (4) and closing of the sample vessel receiver (3) or after introduction of the sample (7) and closing of an incubation chamber, the closure unit (10) remains locked by the safety lock (9) until the analysis unit (21) determines that the sample inactivation was successful.

2. The incubator (1) as claimed in claim 1, further comprising a controller (8) for establishing at least one program, wherein, the closure unit (10), after introduction of the sample vessel (4) and closing of the sample vessel receiver (3) or after introduction of the sample (7) and closing of an incubation chamber, remains locked by the safety lock (9) until at least one of the established program has ended or an opening code has been input by an authorized user.

3. The incubator (1) as claimed in claim 1, wherein the at least one measurement apparatus (11) carries out a measurement of at least one experimental parameter within a sample vessel (4) inserted into the sample vessel receiver (3), the at least one measurement apparatus (11) is set up to determine at least one experimental parameter, wherein the at least one experimental parameter is at least one of: optical density, color reaction, impedance, pH, gas composition, oxygen content or $CO_2$ content, in at least one of liquid or supernatant, spectroscopic property, electrochemical property, reaction of at least one of a substrate or a chemical, fluorescence, luminescence, nucleic acids, a nucleic acid sequence, cell mass, peptides, or proteins, and wherein the at least one measurement apparatus (11) is at least one of: a chromatography unit, a mass spectrometer, a lateral flow test unit, a spectroscopy unit, a fluorescence measurement unit, a luminescence measurement unit, a capillary electrophoresis unit, a protein characterization unit, a nucleic acid characterization unit, a immunoassay unit, or an immuno-beads unit.

4. The incubator (1) as claimed in claim 1, further comprising a viewing window (14) through which optical measurement on the sample (7) is possible within at least one of the sample vessel receiver (3) or within the sample receiver, and an optical sensor (15) for performing an optical measurement on or in the sample (7).

5. The incubator (1) as claimed in claim 1, wherein the sample inactivation device (6) inactivates the sample (7) by at least one of: physical, mechanical, thermal, chemical, biological or radiation-generated inactivation, and wherein the sample inactivation device (6) is configured as at least one of: an autoclave, a hot air sterilizer, a gassing unit, a irradiation unit, a microwave unit, an electron beam unit, an ultrasound unit, a vacuum unit, a cavitation unit, a shear force unit or an inactivator release unit.

6. An incubator (1) for at least one of cultivation of microorganisms (2) or performance of a chemical reaction, the incubator comprising:

a sample receiver into which a sample (7) is directly introducible;

a heating device (5) for changing a temperature in the sample receiver;

a sample inactivation device (6) for inactivating the sample (7) in the sample receiver;

an analysis unit (21), comprising at least one measurement apparatus (11) having a sensor or probe extending into the sample receiver, to determine if the inactivation of the sample by the sample inactivation device (6) was successful; and a closure unit (10) of the incubator (1) comprising a safety lock (9) wherein after introduction of the sample (7) and closing of an incubation chamber, the closure unit (10) remains locked by the safety lock (9) until the analysis unit (21) determines that the sample inactivation was successful.

* * * * *